United States Patent

Hideg et al.

[11] 4,017,507
[45] Apr. 12, 1977

[54] 2,3-DIHYDRO-7-CHLOROTHIAZOLO[3,2-A]BENZIMIDAZOLE AND SALT

[75] Inventors: Kalman Hideg; Olga Hankovszky, both of Pecs; Eva Palosi, Budapest; Gyorgy Hajos, Budapest; Laszlo Szporny, Budapest, all of Hungary

[73] Assignee: Richter Gedeon Vegyeszeti Gyar Rt., Budapest, Hungary

[22] Filed: Dec. 5, 1975

[21] Appl. No.: 637,978

Related U.S. Application Data

[62] Division of Ser. No. 473,184, May 24, 1974, Pat. No. 3,932,395.

[30] Foreign Application Priority Data

June 20, 1973 Hungary .............................. RI 509

[52] U.S. Cl. ........................................ 260/306.7 T
[51] Int. Cl.$^2$ ........................................ C07D 513/04
[58] Field of Search ............................ 260/306.7 T

[56] References Cited

UNITED STATES PATENTS 3,932,395  1/1976  Hideg et al. ................ 260/306.7 T

OTHER PUBLICATIONS

Mukherjee et al., *Chem. Abstracts,* 59:15275h (1963).

*Primary Examiner*—R. Gallagher
*Attorney, Agent, or Firm*—Toren, McGeady and Stanger

[57] ABSTRACT

New tricyclic fused imidazole derivatives of the general formula (I),

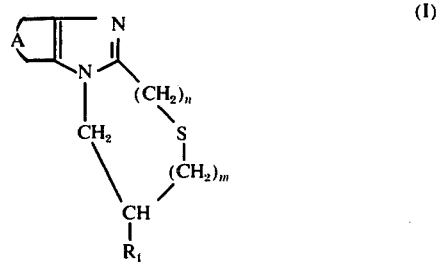

(I)

wherein
R$_1$ stands for hydrogen or hydroxy,
n is equal to zero or one,
m is equal to zero, one or two,
A stands for a group of the general formula (II),

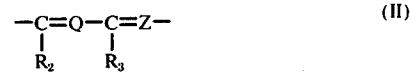

(II)

wherein
R$_2$ represents hydrogen or hydroxy,
R$_3$ represents hydrogen or amino, or
Q and Z each stand for nitrogen or a=C— group, or
A stands for a group of the general formula (III),

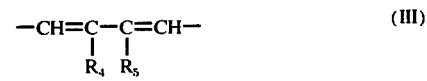

(III)

wherein
R$_4$ and R$_5$ each represent hydrogen, methyl, chlorine or nitro, were prepared by reacting a compound of the general formula (IV)

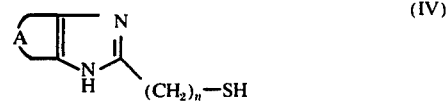

(IV)

wherein A and n each have the same meanings as defined above, with a compound of the general formula (V),

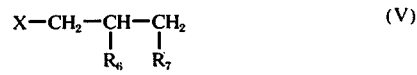

(V)

wherein X stands for halogen, R$_6$ stands for hydrogen and R$_7$ stands for a group of the general formula (VI),

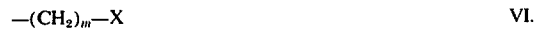

VI.

in which m and X each have the same meanings as defined above, or R$_6$ and R$_7$ together stand for oxygen. The reaction is carried out optionally in the presence of a base. The compounds of the general formula (I) can be converted into their acid addition salts.

The compounds of the general formula (I) as well as their acid addition salts exert antipyretic and antiphlogistic activities, inhibit the reproduction of viruses, and exert a protecting effect against albumine shock.

1 Claim, No Drawings

2,3-DIHYDRO-7-CHLOROTHIAZOLO[3,2-a]BENZIMIDAZOLE AND SALT

This is a division of application Ser. No. 473,184 filed May 24, 1974, now U.S. Pat. No. 3,932,395.

This invention relates to new tricyclic fused imidazole derivatives and acid addition salts thereof, and a process for the preparation of these compounds.

The compounds according to the invention correspond to the general formula (I)

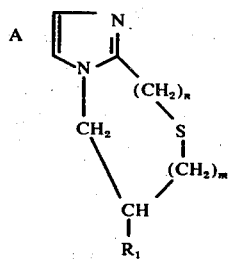

wherein
$R_1$ stands for hydrogen or hydroxy,
$n$ is equal to zero or one,
$m$ is equal to zero, one or two,
A stands for a group of the general formula (II).

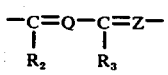

wherein
$R_2$ represents hydrogen or hydroxy,
$R_3$ represents hydrogen or amino, and
Q and Z each stand for nitrogen or a =CH- group, or
A stands for a group of the general formula (III),

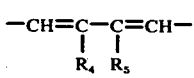

wherein $R_4$ and $R_5$ each represent hydrogen, methyl, chlorine or nitro.

We have found that the compounds of the general formula (I) possess valuable pharmacological properties. More particularly, these compounds exert antipyretic and antiphlogistic activities, inhibit the reproduction of viruses, and exert a protecting effect against albumine shock.

As regards the antipyretic and antiphlogistic activities, compounds of the general formula (I), wherein A stands for a group of the general formula (II) and $R_2$ and $R_3$ each represent hydrogen or $R_2$ stands for hydroxy and $R_3$ stands for amino, or A represents a group of the general formula (III), wherein $R_4$ and $R_5$ are the same and stand for hydrogen of methyl, are the most advantageous ones. Of these compounds 3,4-dihydro-2H-(1,3)-thiazino[3,2-a]pyrido[3,2-d]imide zole is the most active one.

A protecting effect against albumine shock is exerted primarily by the compounds that contain a group of the general formula (III) as A substituent and hydroxy as $R_1$ substituent. Of these compounds 3,4-dihydro-3-hydroxy-2H-(1,3)-thiazino[3,2-a]benzimidazole proved to be the most active one.

As regards the inhibiting effect exerted on the reproduction of viruses, compounds of the general formula (I) wherein $R_1$ stands for hydroxy proved to be the most advantageous. In this group 3,4-dihydro-3-hydroxy-7,8-dimethyl-2H-(1,3)-thiazino[3,2-a]benzimidazole shows the most potent effect.

The antipyretic effect of the compounds was examined according to the method of Winder (C. V. Winder et. al.: Pharmac. exp. Ther. 138, 405 (1963)). A 15% yeast suspension was administered in a dosage of 1 ml./100 g. body weight to male rats each weighing 210 ± 10 g. No food was given to the animals, they could consume water, however, ad libitum. 16 hours after the administration of yeast, the body temperature of the animals was taken, and the compound to be tested was administered into the animals orally through a tube. Thereafter the change in rectal temperature of the animals was recorded for 5 hours, using an "Elab" type electrothermometer. During this period no water was given to the animals. The results of the experiments carried out with 3,4-dihydro-2H-(1,3)-thiazino[3,2-a]pyrido[3,2-d]imidazole are summarized in Table 1. As the reference substance, phenacetine, a widely applied antipyretic was used.

Table 1

| Substance | Dosage mg./kg. | Temperature change observed 1 2 3 4 5 hours after treatment, °C | | | | |
|---|---|---|---|---|---|---|
| 3,4-dihydro-2H-(1,3)-thiazino-[3,2-a]pyrido-[3,2-d]imidazole | 60 | −1.2 | −1.1 | −1.0 | −0.5 | −0.6 |
|  | 120 | −1.8 | −1.4 | −1.8 | −1.8 | −1.1 |
| Phenacetine | 60 | −1.3 | −1.2 | −1.5 | −0.7 | −1.0 |
|  | 120 | −1.7 | −2.1 | −2.4 | −1.6 | −1.4 |

The protecting effect against the anaphylaxic shock caused by albumine was examined by Herxheimer's method (N. Herxheimer and E. Szersemann: Arch. int. Pharmacodyn. 125, 265 (1960). Guinea pigs, each weighing 300 to 400 g., were senzibilized by the intraperitoneal administration of a 5% eggalbusine solution. This treatment was repeated on the next day. Two weeks after the senzibilization a 5% albumine solution was inhalated by the animals in the form of an aerosol, and the time elapsed until the development of shock was measured. The compound to be tested was administered intraperitoneally in a dosage of 20 mg./kg. 30 minutes before the aerosol treatment. The test was carried out on groups each consisting of 6 animals. The animals showing no dyspnoe for 10 minutes were considered as being protected. In this test 3,4-dihydro-3-hydroxy-2H-(1,3)-thiazino[3,2-a]benzimidazole, in a dosage of 20 mg./kg., exerted a protective effect of 80%. The $ED_{50}$ value of theophylline was 17 mg./kg. in the same test. On the basis of these results 3,4-dihydro-3-hydroxy-2H-(1,3)-thiazino[3,2-a]benzimidazole can be regarded as an active therapeutic for the treatment of bronchial asthma.

The inhibiting effect exerted on virus reproduction was examined by the plaque method (S. Pácsa, O. Hankovszky, K. Hideg: Acta microbiol. Acad. Sci Hung. 12, 215 /1965/; S. Pácsa, O. Hankovszky, K. Hideg: Nature 208, 409 /1965/). The tests were carried out on HEp-2 cell cultures propagated in a McCoy culture liquid containing 10% of inactivated bovine serum. Monolayers of the culture were formed by introducing $5 \times 10^5$ or $10^6$ HEP-2 cells per dish into Petri dishes of 3 cm. or 5 cm. diameter, respectively, and incubating the system for 2 to 3 days at 37° C. Thereafter the culture liquid was removed and the monolayers were inoculated with 20 to 150 PFU (plaque forming units) of a polio 1 virus of Mahoney strain. After an absorption period of one hour at room temperature the cell cultures were covered with F-11 culture liquid containing agar and 0.5% of bovine serum. 4 to 8 Petri dishes were used for the examination of each compound, adding the compounds in different concentrations to the individual dishes. The results were evaluated on the third and fourth days of incubation. In this test the inhibiting effect of 3,4-dihydro-3-hydroxy-7,8-dimethyl-2H-(1,3)-thiazino[3,2-a]benzimidazole varied between 50 to 95%, depending on the concentration.

The compounds of the general formula (I), wherein $R_1$, $n$, $m$, and A each have the same meanings as defined above, and the acid addition salts thereof can be prepared according to the invention by reacting a compound of the general formula (IV)

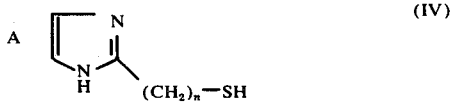

wherein A and $n$ each have the same meanings as defined above, with a compound of the general formula (V),

wherein X stands for halogen, $R_6$ stands for hydrogen and $R_7$ stands for a group of the general formula (IV),

in which $m$ and X each have the same meanings as defined above, or $R_6$ and $R_7$ together stand for oxygen, optionally in the presence of a base, preferably an alkali or alkaline earth metal hydroxide, and if desired, converting the obtained free bases into their acid addition salts, or alternately, converting the obtained salts into the free bases, and, if desired, separating the isomeric mixtures formed optionally into the pure isomers.

The compounds of the general formula (IV) may also exist in their tautomeric forms, obtained by the migration of the hydrogen atom to the other nitrogen atom of the imidazole ring and the simultaneous rearrangement of the double bond. Such a tautomeric rearrangement occurs when e.g. the hydrogen attached to the sulfur atom of the side chain migrates to the nitrogen of the ring, and the double bond is shifted simultaneously between the sulfur atom and the adjacent carbon atom. The thus formed thione compound is rearranged thereafter into the more stable thiol form, but in this rearrangement either of the hydrogens attached to the ring nitrogens may migrate to the sulfur atom. As a consequence of these rearrangement reactions, the compound of the general formula (IV) may exist in the form of two isomeric thiols.

If group A is symmetric, that is, the $R_2$, $R_3$ and Q, Z pairs in formula (II), or the $R_4$, $R_5$ pair in group (III) have the same meaning, the tautomeric thiol forms are the same in structure, i.e., the tautomery is only apparent. Otherwise, i.e., when group A is asymmetric, the compounds of the general formula (IV) exist in the form of two isomeric thiols, in a concentration ratio depending on the tautomeric equilibrium constant.

If the starting compounds of the general formula (IV) contain an asymmetric A substituent, the end-products of the general formula (I) obtained therefrom may also be mixtures of two isomers with the same empirical formula.

Groups (II) and (III), represented by substituent A, may be attached to the imidazole ring in compounds (I) and (IV) in two ways, and these two possibilities represent the structures of the isomers existing as a consequence of the above tautomeric rearrangement.

For the sake of clarity, each of the compounds (IV) and (I) that conatin an asymmetric A substituent is referred to in the specification and the claims as a single compound, under the name of the isomeric form that is more probable on the basis of the inductive effects of the substituents.

The acid binding agent and the reactant of the general formula (V) can be added to the reaction mixture in any desired sequence. Preferably, the base acting as acid binding agent is added first, and then the reactant of the general formula (V) is added.

The organic or mineral base can be administered in solid state or in the form of a solution or suspension formed with water or an aqueous organic solvent.

According to an advantageous method of the invention the separation of the halide salt by-product in the form of an insoluble precipitate from the end-product is promoted by an appropriate ratio of water and the organic solvent.

The reaction of the compound having the general formula (IV) with a compound of the general formula (V) in the presence of an acid binding agent is generally carried out at elevated temperatures, preferably at the boiling point of the reaction mixture. The reaction is completed when the inorganic halide ceases to separate.

As acid binding agent, preferably an alkali or alkaline earth metal hydroxide, such as sodium hydroxide, potassium hydroxide, hydrated lime oxide, etc. is used.

The compounds of the general formula (I) can be separated from the halide salt by-product e.g. by filtration or centrifugation. Thereafter the solvent is removed from the solution containing the end-product preferably by evaporation to dryness under reduced pressure. If desired, the thus-obtained free base can be purified, e.g., by recrystallization from a suitable solvent, such as, an alcohol, acetone, ether, etc.

Any of the free bases of the general formula (I) can be converted into its acid addition salt by reacting it with an appropriate organic or mineral acid.

The salt formation can be carried out directly in the reaction mixture where the bases of the general formula (I) were formed. In this instance, the end-products are separated in the form of their salts formed with mineral or organic acids.

The optionally formed isomeric mixtures or acid addition salts thereof can be separated by known methods to yield the individual isomers in pure state. The separation methods are based on the differences in the physical or chemical properties of the respective isomers.

The compounds of the invention can be converted into pharmaceutical products using organic or mineral carriers which are inert towards the active agents and suitable for enteral or parenteral administration.

The pharmaceutical compositions may contain the new compounds of the general formula (I) either alone or in combination with other known active agents.

If desired, the pharmaceutical products can be sterilized or admixed with other auxiliary substances, such as, salts influencing the osmotic pressure, buffers, etc.

The invention is elucidated in detail by the aid of the following non-limiting Examples.

EXAMPLE 1

3,4-Dihydro-2H-(1,3)-thiazino[3,2-a]benzimidazole 15.0 g. (0.1 moles) of 2-mercapto-benzimidazole are suspended in 100 ml. of alcohol, and a solution of 8 g. (0.2 moles) of sodium hydroxide in 10 ml. of water is added. Thereafter 15.7 g (0.1 moles) of 1,3-chlorobromo-propane are added to the obtained solution, and the mixture is refluxed for about 3 hours. At the end of the reaction the mineral salts cease to separate.

The separated mineral salts are removed by filtration and washed with a minimum amount of alcohol. The combined filtrate and wash is evaporated to dryness under reduced pressure to yield 12.0 g. (63%) of 3,4-dihydro-2H-(1,3)-thiazino[3,2-a]benzimidazole; m.p.: 146°–147° C (heating rate: 4° C/min.) After recrystallization from alcohol, the product melts at 147°–148° C.

Analysis: Calculated for $C_{10}H_{10}N_2S$ (190.26): C: 63.13%; H: 5.30%; N: 14.72%; S: 16.85%; Found: C: 63.15%; H: 5.36%; N: 14.70%; S: 16.20%.

EXAMPLE 2

3,4-Dihydro-2H-(1,3)-thiazino[3,2-a]benzimidazole hydrochloride

The base obtained as described in Example 1 is dissolved in a mixture of alcohol and acetone, and the solution is acidified to pH 3 with hydrochloric acid. The separated crystals are filtered off, washed and dried. This way 15.7 g. (90%) of 3,4-dihydro-2H-(1,3)-thiazino[3,2-a]benzimidazole hydrochloride are obtained; m.p.: 198°–199° C.

Analysis: Calculated for $C_{10}H_{10}N_2S.HCl$ (226.73): C: 52.98%; H: 4.89%; N: 12.36%; S: 14.14%; Cl:15.63%; Found: C: 53.05%; H: 5.20%; N: 12.13%; S: 14.00%; Cl:15.93%.

NMR-spectrum (in $D_2O$):

7.25 (2H, m, =N-CH$_2$-CH$_2$-CH$_2$-S-)
6.30 (2H, t, =N-CH$_2$-CH$_2$-CH$_2$-S-)
5.52 (2H, t, =N-CH$_2$-CH$_2$-CH$_2$-S-)
2.34 (4H, s, aromatic protons)

EXAMPLE 3

4,5-Dihydro-1H,3H-(1,4)-thiazepino[4,3-a]benzimidazole 16.4 g. (0.1 moles) of 2-mercapto-methylene-benzimidazole are dissolved in 100 ml of methanol, and 11.2 g. (0.2 moles) of potassium hydroxide dissolved in a small amount of methanol are added, followed by 15.7 g. (0.1 moles) of 1,3-chlorobromo-propane. The reaction mixture is refluxed for 3 hours. At the end of the reaction, the mineral salts cease to separate.

The product is separated as described in Example 1. 15.1 g. (74%) of 4,5-dihydro-1H,3H-(1,4)-thiazepino[4,3-a]-benzimidazole are obtained; m.p.: 155°–157° C (heating rate: 4° C/min.)

Analysis: Calculated for $C_{11}H_{12}N_2S$ (204.29): C: 64.67%; H: 5.92%; N: 13.17%; S: 15.70%; Found: C: 64.55%; H: 5.55%; N: 13.15%; S: 15.44%.

EXAMPLE 4

4,5-Dihydro-1H,3H-(1,4)-thiazepino[4,3-a]benzimidazole hydrochloride

One proceeds as described in Example 2 with the difference that the base obtained in Example 3 is used as a starting substance. The product melts at 172°–174° C (heating rate: 4° C/min.)

Analysis: Calculated for $C_{11}H_{12}N_2S.HCl$ (240.75): C: 53.88%; H: 5.44%; N: 11.63%; S: 13.32%; Cl: 14.73%; Found: C: 54.66%; H: 5.50%; N: 11.90%; S: 13.25%; Cl: 14.44%.

EXAMPLE 5

3,4-Dihydro-3-hydroxy-7,8-dimethyl-2H-(1,3)-thiazino-[3,2-a]benzimidazole 17.8 g. (0.1 moles) of 2-thio-5,6-dimethyl-benzimidazole are suspended in 150 ml of ethanol, and a solution of 4.0 g. (0.1 moles]of sodium hydroxide formed with 10 to 15 ml. of water is added. 9.2 g. (0.1 moles) of epichlorohydrine are added to the obtained solution, and the reaction mixture is refluxed for 3 hours.

The reaction mixture is processed as described in Example 1 to yield 20.3 g. (87%) of 3,4-dihydro-3-hydroxy-7,8-dimethyl-2H-(1,3)-thiazino[3,2-a]benzimidazole; m.p: 266°–267° C (heating rate: 4° C/min.).

Analysis: Calculated for $C_{12}H_{14}N_2OS$ (234.32): C: 61.51%; H: 6.02%; N: 11.96%; S: 13.69%; Found: C: 61.56%; H: 6.13%; N: 12.00%; S: 13.36%.

NMR- spectrum (in trifluoroacetic acid):

7.48 (CH, S, -/CH$_3$/$_2$)

6.20 (2H, m, =N—CH$_2$—CH—CH$_2$—S—)

5.30 to 5.50 (2H, m, =N—CH$_2$—CH—CH$_2$—S—)

4.65 to 4.85 (1H, m, =N—CH$_2$—CH—CH$_2$—S—)

2.50 (1H, s, aromatic proton)
2.58 (1H, s, aromatic proton)

EXAMPLE 6

3,4-Dihydro-3-hydroxy-7,8-dimethyl-2H-(1,3)-thiazino[3,2-a]benzimidazole hydrochloride One proceeds as described in Example 2 with the difference that the compound obtained according to Example 5 is used as starting substance. The product melts at 272°–274° C (heating rate: 4° C/min.).

Analysis: Calculated for $C_{12}H_{14}N_2OS.HCl$ (270.78): C: 53.23%; H: 5.58%; N: 10.35%; S: 11.84%; Cl: 13.10%; Found: C: 53.24%; H: 6.01%; N: 10.54%; S: 12.07%; Cl: 13.14%.

In the following Examples, the bases are prepared as described in Examples 1, 3 or 5, while the acid addition salts are prepared as described in Example 2.

EXAMPLE 7

2,3-Dihydro-(1,3)-thiazole[3,2-a]benzimidazole

The compound melts at 239°–240° C (heating rate: 4° C/min.).

Analysis: Calculated for $C_9H_8N_2S$ (178.12): C: 61.34%; H: 4.57%; N: 15.90%; S: 18.19%; Found: C: 60.59%; H: 4.60%; N: 15.69%; S: 18.62%.

EXAMPLE 8

2,3-Dihydro-(1,3)-thiazole[3,2-a]benzimidazole hydrochloride

The compound melts at 217°–219° C (heating rate: 4° C/min.).

Analysis: Calculated for $C_9H_8N_2S \cdot HCl$ (212.70): C: 50.82%; H: 4.26%; N: 13.17%; S: 15.08%; Cl: 16.67%; Found: C: 50.75%; H: 4.39%; N: 13.17%; S: 14.83%; Cl: 16.84%.

NMR-spectrum (in $D_2O$): 6.07 (4H, s, $-\underline{CH_2}-\underline{CH_2}-$), 2.40 (4H, s, aromatic protons)

EXAMPLE 9

4,5-Dihydro-2H,3H-1,3)-thiazepino[3,2-a]benzimidazole hydrochloride

The compound melts at 128°–129° C (heating rate: 4° C/min.).

Analysis: Calculated for $C_{11}H_{12}N_2S \cdot HCl$ (240.75): C: 54.88%; H: 5.44%; N: 11.64%; S: 13.32%; Cl: 14.72%; Found: C: 54.30%; H: 5.24%; N: 11.72%; S: 13.28%; Cl: 15.10%.

EXAMPLE 10

3,4-Dihydro-3-hydroxy-2H-(1,3)-thiazino[3,2a]benzimidazole

The compound melts at 214°–215° C (heating rate: 4° C/min.).

Analysis: Calculated for $C_{10}H_{10}N_2S$ (206.26): C: 58.23% H: 4.89% N: 13.58% S: 15.54% Found: C: 58.33% H: 5.21% N: 13.42% S: 15.22%

NMR-spectrum (in trifluoroacetic acid):

---

6.20 (2H, m, $=N-CH_2-\overset{|}{CH}-\underline{CH_2}-S-$)

5.36 (2H, m, $=N-\underline{CH_2}-\overset{|}{CH}-CH_2-S-$)

4.75 (1H, m, $=N-CH_2-\underline{CH}-CH_2-S-$)

2.83 (4H, s, aromatic protons)

---

EXAMPLE 11

3,4-Dihydro-3-hydroxy-2H-(1,3)-thiazino[3,2-a]benzimidazole hydrochloride

The compound melts at 211-212° C (heating rate: 4° C/min).

Analysis: Calculated for $C_{10}H_{10}N_2S \cdot HCl$ (242.73) C: 49.48%; H: 4.57%; N: 11.54%; S: 13.21%; Cl: 14.61%; Found: C: 49.44%; H: 4.93%; N: 11.44%; S: 13.37%; Cl: 14.45%.

NMR:spectrum (in $D_2O$):

6.22 (2H, t, $=N-CH_2-\overset{|}{CH}-\underline{CH_2}-S-$)

5.46 (2H, t, $=N-\underline{CH_2}-\overset{|}{CH}-CH_2-S-$)

4.95 (1H, m, $=N-CH_2-\underline{CH}-CH_2-S-$)

2.33 (4H, s, aromatic protons)

---

EXAMPLE 12

4,5-Dihydro-4-hydroxy-1H,3H-(1,4)-thiazepino[4,3-a]benzimidazole

The compound melts at 231°–233° C (heating rate: 4° C/min.)

Analysis: Calculated for $C_{11}H_{12}N_2OS$ (220.29) C: 59.97%; H: 5.49%; N: 12.72%; S: 14.56%; Found: C: 60.44%; H: 5.47%; N: 12.76%; S: 14.20%.

NMR spectrum (in trifluoroacetic acid):

---

6.48 (2H, m, $=N-CH_2-\overset{|}{CH}-\underline{CH_2}-S-$)

5.58 (2H, s, $-\underline{CH_2}-S-$)

4.80 to 5.38 (3H, m, $=N-\underline{CH_2}-\overset{|}{CH}-CH_2-S-$)

2.20 (4H, s, aromatic protons)

---

EXAMPLE 13

4,5-Dihydro-4-hydroxy-1H,3H-(1,4)-thiazepino[4,3-a]benzimidazole hydrochloride

The compound melts at 191°–192° C (heating rate: 4° C/min.)

Analysis: Calculated for $C_{11}H_{12}N_2OS \cdot HCl$ (256.75): C: 51.46%; H: 5.10%; N:10.91%; S:12.49%; Cl:13.81%; Found: C: 50.96%; H: 5.46%; N:10.85%; S:12.53%; Cl:13.36%.

EXAMPLE 14

3,4-Dihydro-7,8-dimethyl-2H-(1,3)thiazino[3,2-a]benzimidazole

The compound melts at 225°–226° C (heating rate: 4° C/min.)

Analysis: Calculated for $C_{12}H_{14}N_2S$ (218.32): C: 66.02%; H: 6.46%; N: 12.83%; S: 14.69%; Found: C: 65.93%; H: 6.54%; N: 12.50%; S: 15.01%.

EXAMPLE 15

3,4-Dihydro-7,8-dimethyl-2H-(1,3)-thiazino[3,2-a]benzimidazole hydrochloride

The compound melts at 218°–220° C (Heating rate 4° C/min.)

Analysis: Calculated for $C_{12}H_{14}N_2S \cdot HCl$ (254.78): C: 56.57%; H: 5.39%; N: 11.00%; S: 12.59%; Cl: 13.91%; Found: C: 56.92%; H: 5.10%; N: 10.85%; S: 12.73%; Cl: 13.61%.

NMR-spectrum (in $D_2O$):

8.72 (6H, s, $/CH_3/_2$)
7.40 to 8.70 (2H, m, $=N-CH_2-\underline{CH_2}-CH_2-S-$)

6.50 (2H, t, =N-CH$_2$-CH$_2$-CH$_2$-S-)
5.85 (2H, m, =N-CH$_2$-CH$_2$-CH$_2$-S-) 2.85 (1H, s, aromatic proton)
2.75 (1H, s, aromatic proton)

EXAMPLE 16

3,4-Dihydro-8,9-dimethyl-2H,2H-(1,3)thiazepino[3,2-a]benzimidazole hydrochloride.

The compound melts at 138°–139° C (heating rate: 4° C/min.).

Analysis: Calculated for C$_{13}$H$_{16}$N$_2$S.HCl (268.81): C: 58.09%; H: 6.37%; N: 10.42%; S: 11.93%; Cl: 13.19%; Found: C: 58.26%. H: 6.45%; N: 10.67%; S: 11.87%; Cl: 13.03%.

EXAMPLE 17

3,4-Dihydro-7-chloro-2H-(1,3)-thiazino[3,2-a]benzimidazole

The compound melts at 178°–179° C (heating rate: 4° C/min.).

Analysis: Calculated for C$_{10}$H$_9$ClN$_2$OS (240.71): C: 49.90%; H: 3.77%; N: 11.64%; S: 13.32%; Cl: 14.73%; Found: C: 50.22%; H: 3.11%; N: 11.97%; S: 13.67%; Cl: 14.28%.

EXAMPLE 18

3,4-Dihydro-2H-(1,3)-thiazino[3,2-a]pyrido[3,2-d]imidazole dihydrochloride

The compond melts at 182°–183° C (heating rate: 4° C/min.).

Analysis: Calculated for C$_9$H$_9$N$_3$S.2HCl (267.17): C: 40.93%; H: 4.19%; N: 15.91%; S: 12.12%; Cl: 26.84%; Found: C: 40.40%; H: 4.40%; N: 16.03%; S: 12.32%; Cl: 26.48%.

NMR-spectrum (in D$_2$O):

7.45 (2H, m, =N-CH$_2$-CH$_2$-S-)
6.46 (2H, m, =N-CH$_2$-CH$_2$-CH$_2$-S-)
5.50 (2H, m, N-CH$_2$-CH$_2$-CH$_2$-S-)
1.50 to 2.50 (3H, pyridine protons)

EXAMPLE 19

3,4-Dihydro-3-hydroxy-2H-(1,3)-thiazino[3,2-a]pyrido[3,2-d]imidazole hydrochloride The compound melts at 183°–185° C (heating rate: 4° C/min.)

Analysis: Calculated for C$_9$H$_9$N$_3$OS.HCl (243.71): C: 44.365; H: 4.13%; N: 17.25%; S: 13.16%; Cl: 14.54%; Found: C: 44.25%; H: 4.10%; N: 17.63%; S: 13.27%; Cl: 14.52%.

EXAMPLE 20

3,4-Dihydro-2H-(1,3)-thiazino[3,2-a]pyrimidino[5,4-d]imidazole

The compound melts at 128°–130° C (heating rate: 4° C/min.).

Analysis: Calculated for C$_8$H$_8$N$_4$S (192.24): C: 49.99%; H: 4.19%; N: 29.14%; S: 16.68%; Found: C: 50.06%; H: 4.37%; N: 29.21%; S: 16.45%.

EXAMPLE 20

3,4-Dihydro-2H-(1,3)-thiazino[3,2-a]pyrimidino[5,4-d]imidazole hydrochloride

The compound melts at 180°–182° C (heating rate: 4° C/min.).

Analysis: Calculated for C$_8$H$_8$N$_4$S.HCl (228.70): C: 42.02%; H: 3.96%; N: 24.50%; S: 14.02%; Cl: 15.50%; Found: C: 42.01%; N: 4.07%; N: 23.90%; S: 14.145; Cl: 15.50%.

NMR-spectrum (in D$_2$O):
7.32 (2H, m, =N-CH$_2$-CH$_2$-CH$_2$-S-)
6.45 (2H, t, =N-CH$_2$-CH$_2$-CH$_2$-S-)
5.38 (2H, t, =N-CH$_2$-CH$_2$-CH$_2$-S-)
0.58 to 0.80 (2H, m, pyrimidine protons)

EXAMPLE 32

3,4-Dihydro-6-hydroxy-8-amino-2H-(1,3)-thiazino[3,2-a]pyrimidino[5,4-d]imidazole The compound melts at 300° C (heating rate: 4° C/min.).

Analysis: Calculated for C$_8$H$_9$N$_5$OS (225.25): C: 43.05%; H: 4.06%; N: 31.37%; S: 14.36%; Found: C: 43.09%; H: 4.17%; N: 30.97%; S: 13.71%.

EXAMPLE 23

3,4-Dihydro-6-hydroxy-8-amino-2H-(1,3)-thiazino[3,2-a]pyrimidino[5,4-d]imidazole hydrochloride The compound melts at 350° C (heating rate: 4° C/min.).

Analysis: Calculated for C$_8$H$_9$N$_5$OS.HCl (259.71): C:37.00%; H: 3.88%; N: 26.97%; S: 12.34%; Cl: 13.65%; Found: C: 36.86%; H: 3.49%; N: 26.89%; S: 12.50%; Cl; 13.34%.

EXAMPLE 24

3,4-Dihydro-3,6-lihydroxy-8-amino-(1,3)-thiazino[3,2-a]pyrimidine[5,4-d]imidazole dihydrochloride The compound melts at 340° C (heating rate: 4° C/min.).

Analysis: Calculated for C$_8$H$_9$N$_5$O$_2$S.2HCl (312.17): C: 30.78%; H: 3.55%; N: 22.43%; S: 10.27%; Cl: 22.72%; Found: C: 30.45%; H: 3.49%; N: 22.60%; S: 9.93%; Cl: 22.23%.

EXAMPLE 25

2,3-Dihydro-7-chloro-(1,3)-thiazolo[3,2-a]benzimidazole hydrochloride

The compound melts at 176°–178° C (heating rate: 4° C/min.)

Analysis: Calculated for C$_9$H$_7$ClN$_2$S.HCl (247.15): C: 43.74%; H: 3.27%; N: 11.33%; S: 12.97%; Cl: 28.69%; Found: C: 43.60%; H: 3.55%; N: 11.20%; S: 12.69%; Cl: 28.82%.

EXAMPLE 26

2,3-Dihydro-7-nitro-(1,3)-thiazolo[3,2-a]benzimidazolehydrochloride

The compound melts at 180°–182° C (heating rate: 4° C/min.).

What we claim is:
1. 2,3-dihydro-7-chloro-(1,3)-thiazolo [3,2-a] benzimidazole or the hydrochloric acid addition salt thereof.

* * * * *